United States Patent
Fallon et al.

[11] Patent Number: 6,027,471
[45] Date of Patent: Feb. 22, 2000

[54] APPARATUS FOR APPLYING A HEMOSTATIC AGENT ONTO A TISSUE

[76] Inventors: Timothy J. Fallon, 406 Bunker Hill St. Apt. #2, Charlestown, Mass. 02129; John G. Maresh, 5380 Medical Dr., #1421, San Antonio, Tex. 78240-1993; James A. Wilkie, 11 Mt. Hood Ter., Melrose, Mass. 02176

[21] Appl. No.: 08/871,178

[22] Filed: Jun. 9, 1997

Related U.S. Application Data

[63] Continuation of application No. 08/373,402, Jan. 18, 1995, abandoned.

[51] Int. Cl.[7] .................................................. A61M 31/00
[52] U.S. Cl. ................................ 604/59; 604/38; 604/60; 606/213
[58] Field of Search .................. 604/11, 59–61, 604/53, 117, 93, 36, 38, 40, 41, 42, 47, 48; 606/213, 214, 229

[56] References Cited

U.S. PATENT DOCUMENTS

| | | | |
|---|---|---|---|
| 3,016,895 | 1/1962 | Sein et al. | 128/217 |
| 3,506,008 | 4/1970 | Huck | 604/60 |
| 3,572,335 | 3/1971 | Robinson | 128/217 |
| 3,667,465 | 6/1972 | Voss | 604/59 |
| 4,738,658 | 4/1988 | Magro et al. | 604/53 |
| 4,790,819 | 12/1988 | Li et al. | 604/59 |
| 4,890,612 | 1/1990 | Kensey | 606/213 |
| 4,900,303 | 2/1990 | Lemelson | 604/54 |
| 4,929,246 | 5/1990 | Sinofsky | 606/8 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,063,025 | 11/1991 | Ito | 422/100 |
| 5,141,515 | 8/1992 | Eberbach | 606/151 |
| 5,292,309 | 3/1994 | Van Tassel et al. | 604/117 |
| 5,310,407 | 5/1994 | Casale | 604/59 |
| 5,391,183 | 2/1995 | Janzen et al. | 606/213 |
| 5,447,499 | 9/1995 | Allaire et al. | 604/42 |
| 5,484,403 | 1/1996 | Yoakum et al. | 604/60 |

FOREIGN PATENT DOCUMENTS

| | | |
|---|---|---|
| 0 308 269 | 9/1988 | European Pat. Off. . |
| 3613762 | 11/1987 | Germany . |
| 92/20312 | 11/1992 | WIPO . |
| 94/28798 | 12/1994 | WIPO . |
| 9428798 | 12/1994 | WIPO . |

OTHER PUBLICATIONS

Fagelman wt al., "A Simple Method for Application of Microfibrillar Collagen," *Surgery, Gynecology & Obstetrics*, 150(6):897 (Jun. 1980).

*Primary Examiner*—Corrine McDermott
*Assistant Examiner*—David J. Cho
*Attorney, Agent, or Firm*—Hamilton, Brook, Smith & Reynolds, P.C.

[57] ABSTRACT

An apparatus and method apply a hemostatic agent onto a tissue. The apparatus includes a tube having a first end and a second end. A lumen of the tube is tapered from the first end to the second end. A hemostatic agent source is within the tube. A plunger is included for directing the hemostatic agent from the tapered tube through an opening at the second end. The hemostatic agent can be directed from the tube through the opening of the second end onto the tissue.

25 Claims, 3 Drawing Sheets

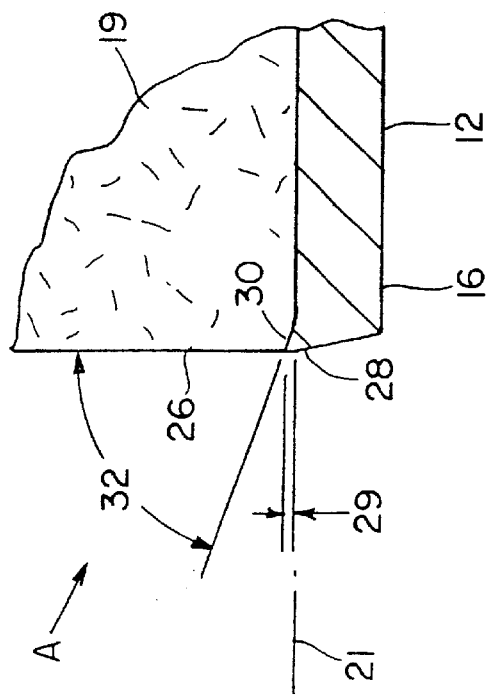
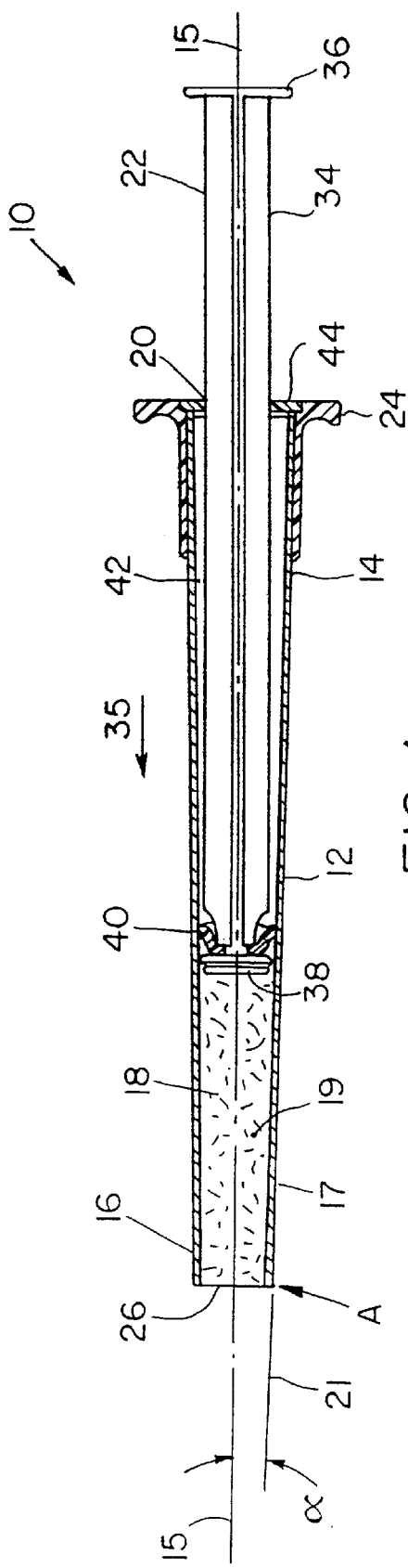
FIG. 1A
FIG. 1

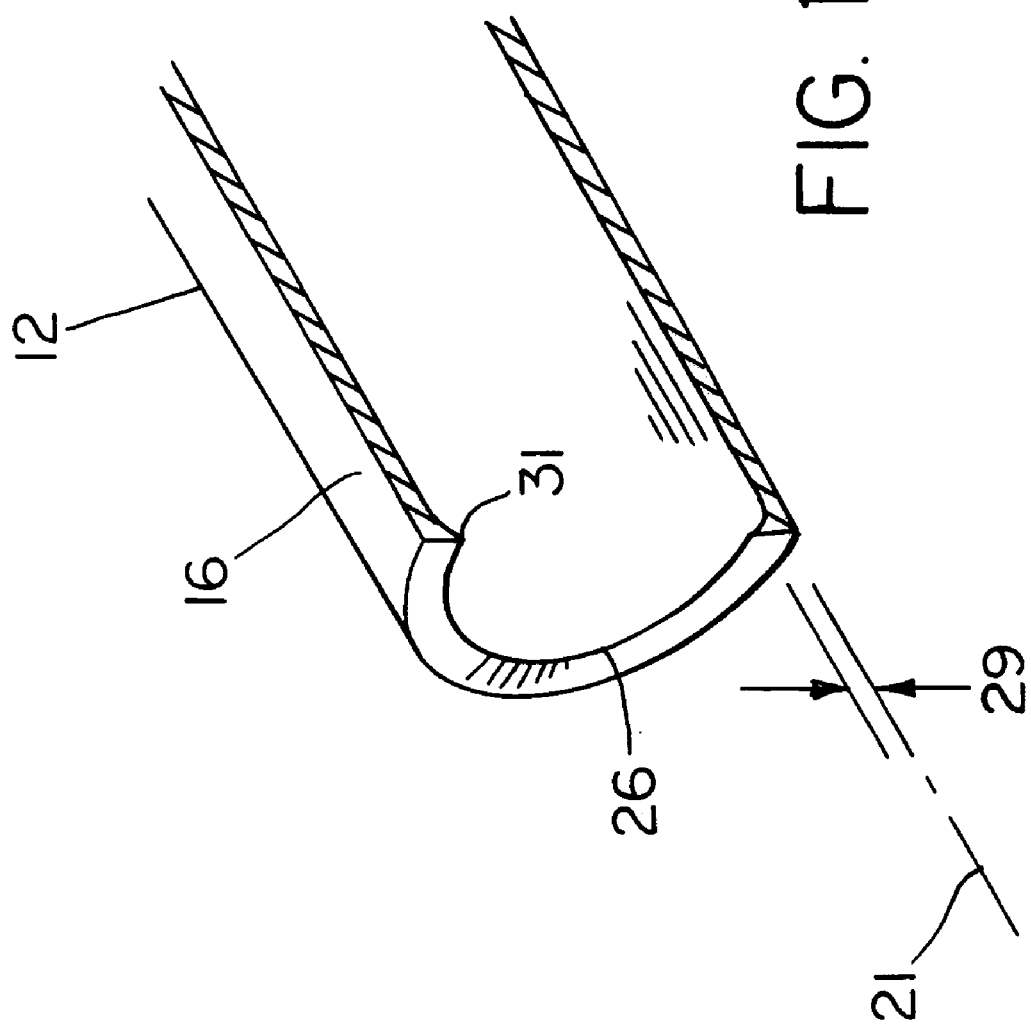

APPARATUS FOR APPLYING A HEMOSTATIC AGENT ONTO A TISSUE

RELATED APPLICATION

This application is a continuation of application Ser. No. 08/373,402, filed on Jan. 18, 1995 now abandoned, which is incorporated herein by reference in its entirety.

BACKGROUND OF THE INVENTION

After tissue has been wounded or cut, the opening must be surgically closed to stop bleeding and enable healing of the tissue. In cases of severe bleeding, one attempt to stem blood loss is the application of a hemostatic agent, such as collagen, from a syringe barrel to the wound to form a wound dressing. The hemostatic agent, on contact with blood, acts to stem bleeding.

However, when the hemostatic material is packaged, over time, shrinkage occurs within the matrix of collagen fibers, often about fifteen percent. This shrinkage can allow the mass of collagen to slide out of the syringe barrel. Further, after a portion of the mass of collagen has been dispersed from the barrel, the remaining amount has a tendency to fall out of the barrel.

In cases of laparoscopic surgery where application of hemostatic agent is necessary, a patient's abdominal cavity is pressurized with gas in order to lift the muscles on the abdominal wall away from the internal organs. A cannula extending through the patient's abdominal wall provides access for instruments, such as syringes, to the abdominal cavity. However, gas often leaks past instruments through a lumen, defined by the cannula, and out of the abdominal cavity, thereby necessitating reinflation of the abdominal cavity.

Therefore, a need exists for an apparatus and method for applying a hemostatic agent to a surface of tissue, which minimizes or overcomes the problems discussed above.

SUMMARY OF THE INVENTION

The present invention relates to an apparatus and method for applying a particulate hemostatic agent onto living tissue.

The apparatus includes a tube having a first end and a second end. A lumen of the tube is tapered from the first end to the second end. A hemostatic agent source is within the tube. Means is included for directing the hemostatic agent from the tapered tube through an opening at the second end. The hemostatic agent can be directed by means for directing from the tapered tube through the opening onto the tissue.

The method includes the steps of placing a tube, being tapered from a first end to a second end, whereby the second end is proximate to the tissue. The tapered tube retains the hemostatic agent within the tube at the second end. A means is controllably actuated at the tube to direct the hemostatic agent through the second end and out of the tube onto the tissue, thereby applying the hemostatic agent onto the tissue.

This invention has many advantages. One of these advantages includes allowing accurate placement by a surgeon of the hemostatic agent onto a bleeding site or within an abdominal cavity. The apparatus also allows for control of the amount of the hemostatic agent applied, while not allowing the hemostatic agent to inadvertently slide out of the tube. The hemostatic agent can be applied within the abdominal cavity without allowing an excess of gas to escape.

BRIEF DESCRIPTION OF THE DRAWINGS

FIG. 1 is an orthogonal projection side view of one embodiment of the apparatus of the present invention.

FIG. 1A is an orthogonal projection side view of Detail A of the embodiment shown in FIG. 1.

FIG. 1B is a perspective view of a cross cut view of a second embodiment in Detail A shown in FIG. 1.

DETAILED DESCRIPTION OF THE INVENTION

Figure 2:
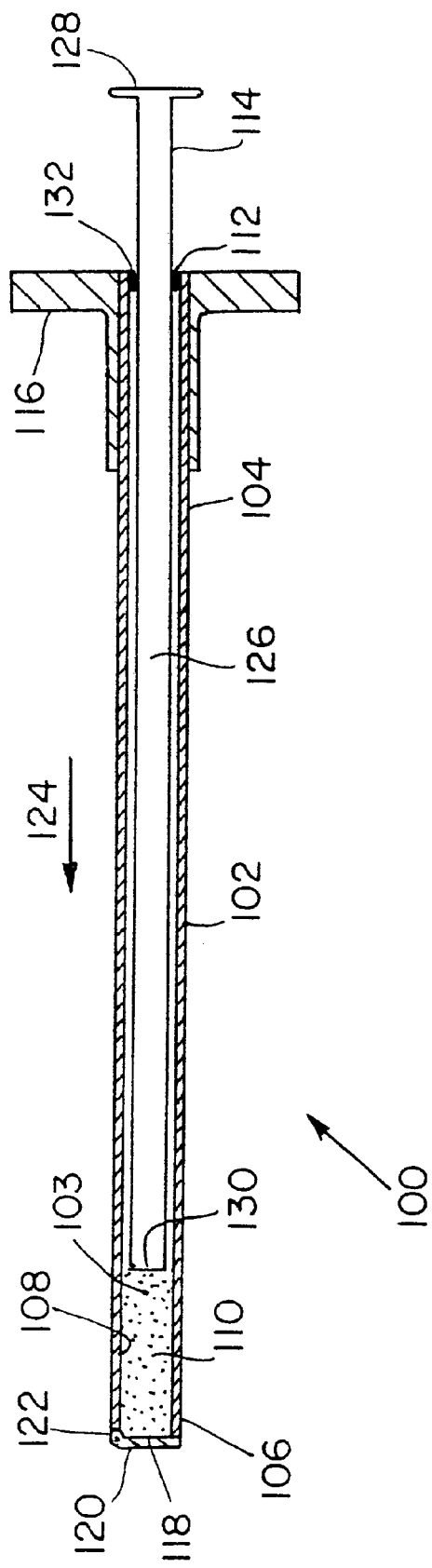
FIG. 2 is an orthogonal projection side view of a second embodiment of the apparatus of the present invention.

The features and other details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principal features of this invention can be employed in various embodiments without departing from the scope of the invention.

One embodiment of the invention, as shown in FIG. 1, a side view, and in FIG. 1A, an enlarged section of FIG. 1, is application device 10, which can be a hand held device. As can be seen in FIG. 1, application device 10 has tapered tube 12 for holding the hemostatic agent. Tube 12 has first end 14 and second end 16. Tube 12 has lumen wall 17, which forms lumen 18 for holding hemostatic agent 19. Lumen wall 17 is tapered from first end 14 to second end 16. The taper is measured by angle a between the longitudinal axis 15 of tube 12 and wall line 21 formed by lumen wall 17 which lies in the same plane as longitudinal axis 15. In one embodiment, lumen 18 has a uniform taper in the range of between about 0.167° and 2°. In a preferred embodiment, tube 12 has a length of about 20 centimeters, a taper of about 0.5° and first end 14 and second end 16 having diameters of about 1.59 and 1.94 centimeters, respectively.

First end 14 of tube 12 has plunger opening 20 for receiving plunger 22 or other means for displacing is hemostatic agent 19 in tube 12. Tube 12 has tube handle 24 for holding the tube at first end 14. Second end 16 has hemostatic agent opening 26 for allowing hemostatic agent 19 to exit application device 10 when a force is applied to hemostatic agent 19 by plunger 22. As shown in FIG. 1A, teeth 28, which are placed about the circumference of hemostatic agent opening 26, form protrusions from tube 12 to assist in hindering hemostatic agent 19 from sliding out of tube 12 through hemostatic agent opening 26. Typically, teeth 28 are uniformly placed around hemostatic agent opening 26. The number of teeth 28 can be one or greater. In one embodiment, four teeth 28 are evenly distributed around hemostatic agent opening 26. Alternatively, as shown in FIG. 1B, ridge 31 can be disposed circumferentially around hemostatic agent opening 26 holding said hemostatic agent in place with tube 12. The ridge can have a height in the range of between about 0.005 and 0.041 centimeters. In another embodiment, teeth 28 can have height 29 in the range of between about 0.005 and 0.041 centimeters and a width in the range of between about 0.013 and 0.152 centimeters. A ratio of the diameter of hemostatic agent opening 26 to the height of teeth 28 can be in the range of between about 7:1 and 320:1. Each of teeth 28 has side 30 with angle 32 from hemostatic agent opening 26. Angle 32 can range from about 10 to 90 degrees. In a preferred embodiment, angle 32 is about 70 degrees.

Referring back to FIG. 1, plunger 22 can slide in direction 35 to displace hemostatic agent 19 from tube 12 through hemostatic agent opening 26. Plunger 22 has shaft 34 with plunger handle 36 at first end 14 and piston 38 near second end 16. Piston 38 is sized to approximate the lumen diameter of tube 12. Seal 40 is affixed to piston 38. Seal 40 prevents hemostatic agent from escaping around piston into space 42 between shaft 22 and lumen wall 17. Seal 40 is formed of a suitable material, such as silicone, to form a seal with the lumen wall 17 but still allow plunger 22 to slide through tube 12. The seal can be a gasket or an o-ring. Further, seal 40 allows a smooth plunger movement by folding back as the plunger slides through tube 12. Alternatively, seal 44 is fixed at first end 14 to prevent gas having a pressure in the range of between about zero and thirty mm Hg from escaping through tube 12.

Application device 10 is composed of materials that can be easily cleaned and sterilized, such as stainless steel or glass. The components of application device 10 are easily disassembled to remove any hemostatic agent deposited within the lumen of application device. Alternatively, application device 10 can be composed of a plastic or other material that is disposable.

Hemostatic agent 19 has particles of hemostatic agents, such as powder or fibers, that are sufficiently small to flow when pressure is applied to hemostatic agent 19 by piston 38 through hemostatic agent opening 26 onto a proximate wound or incision. Hemostatic agent opening 26 is positioned proximate to the surface of the tissue so that the hemostatic agent can then be directed from hemostatic agent opening 26 over the wound or incision, thereby forming a coating of hemostatic agent. In one embodiment, hemostatic agent 19 in application device 10 has a density of about 0.08 g/cm$^3$.

A wide variety of hemostatic agents can be used with this invention. For example, the hemostatic agent can include microfibrillar fibers which act as physiological agents to stop bleeding of living tissue. Examples of a suitable hemostatic agent include collagen, nonsoluble polysaccharide, cellulose and dried gelatin. Collagen can be obtained from many mammalian sources, such as from the hides of cows, pigs, sheep, goats, etc. The hemostatic agent can be in the form of fibers, non-woven web, powder, flakes, particles, milled fibrillar particles, etc. Generally, the density of the hemostatic agent is in the range of between about 0.08 and 0.24 g/cm$^3$. A particularly suitable collagen hemostatic agent is commercially available as AVITENE® fibrillar hemostatic agent, from MedChem Products, Inc., Woburn, Mass.

A second embodiment of the invention, as shown in FIG. 2, a side view, is scopic device 100, which can be a hand held and inserted through a cannula for applying a hemostatic agent directly to an internal tissue site. Tube 102 is for holding hemostatic agent 103. Tube 102 has first end 104 and second end 106. Tube has lumen wall 108, which forms lumen 110. Lumen 110 can be tapered or uniform. In one embodiment, lumen 110 has a diameter in the range of between about four and ten millimeters.

First end 104 of tube 102 has plunger opening 112 for receiving plunger 114 or other means for displacing hemostatic agent 103 in tube 102. Tube 102 has tube handle 116 for holding the tube at first end 104. Second end 106 has hemostatic agent opening 118 for allowing hemostatic agent 103 to exit scopic device 100 when a force is applied to hemostatic agent 103 by plunger 114. Hemostatic agent opening 118 can have a displaceable cover 120 that can swing open about hinge 122 during displacement of hemostatic agent 103. Displaceable cover 120 and hinge 122 can be spring loaded or connected to plunger 114 to control opening. Plunger 114 can slide in direction 124 to displace hemostatic agent 103 from tube 102. Plunger 114 has shaft 126 with plunger handle 128 at first end 104 and piston 130 near second end 106. Piston 130 is sized to approximately the lumen diameter of tube 102. Seal 132 is fixed at first end 104 to prevent gas from escaping through plunger opening 112. Further, seal 132 allows a smooth controlled plunger movement. Alternatively, seal 132 can be positioned along plunger 114. Seal 132 is formed of a suitable material, such as silicone, to form a seal between lumen wall 108 and piston 130 but still allow plunger 114 to slide through tube 102. Seal 132 helps prevent gas having a pressure in the range of between about zero and thirty mm Hg from escaping through tube 102 in order to maintain pressure within the body cavity.

Scopic device 100 can be composed of the same materials as application device 10 and employ the same hemostatic agents. Application device 10 with teeth preferably uses a powder while scopic device can employ either a powder or a non-woven web of a hemostatic agent, such as collagen.

Returning to FIG. 1, hemostatic agent opening 26 on second end 16 of tube 12 is placed proximate to tissue. Lumen wall 17 in tube is tapered from first end 14 to second end. Tube 12 retains hemostatic agent 19 within the tube at second end 16.

Plunger 22 is actuated by applying a force to plunger handle 36 while holding tube 12 in place at tube handle 24 to cause plunger 22 to move in direction 35 relative to tube 12. Hemostatic agent 19 is directed by plunger 22 from tube 12 through hemostatic agent opening 26 onto the tissue.

Equivalents

Those skilled in the art will recognize, or be able to ascertain using no more than routine experimentation, many equivalents to the specific embodiments of the invention described specifically herein. Such equivalents are intended to be encompassed in the scope of the claims.

What is claimed is:

1. An apparatus for applying a hemostatic agent onto a tissue, comprising:

a) a tube having a first end and a second end, said tube defining a lumen that is tapered uniformly from said first end to said second end;

b) a hemostatic agent within said tube;

c) a plunger for directing said hemostatic agent from said tube through an opening at said second end, wherein said hemostatic agent can be directed from the tube through said opening onto the tissue; and d) a seal to prevent passage of the hemostatic agent from said tube between said plunger for directing the hemostatic agent from the tube and said lumen.

2. The apparatus of claim 1 wherein said lumen is tapered at an angle in a range of between about 0.167 and 2 degrees.

3. The apparatus of claim 1 wherein said opening of said second end has at least one tooth disposed around the opening for holding said hemostatic agent in place within said tube until plunger for directing said hemostatic agent from said tube is applied to said hemostatic agent.

4. The apparatus of claim 1 wherein a ridge is disposed circumferentially around the opening for holding said hemostatic agent in place within said tube until plunger for directing said hemostatic agent from said tube is applied to said hemostatic agent.

5. An apparatus for applying a hemostatic agent onto a tissue, comprising:

a) a tube having a first end and a second end, wherein a lumen of said tube is tapered from said first end to said second end;

b) a hemostatic agent source within said tube; and c) a plunger for directing said hemostatic agent from said tapered tube through an opening at said second end, wherein said hemostatic agent can be directed from the tapered tube through said opening onto the tissue.

6. The apparatus of claim 5 wherein said lumen of said tube has a taper with an angle in the range of between about 0.167 and 2 degrees.

7. The apparatus of claim 6 wherein said lumen of said tube has a taper of about 0.5 degrees.

8. The apparatus of claim 5 wherein said opening of said second end has at least one tooth disposed around the opening for holding said hemostatic agent in place within said tube until plunger for directing said hemostatic agent from said tube is applied to said hemostatic agent.

9. The apparatus of claim 8 wherein said teeth are distributed uniformly and circumferentially around the opening.

10. The apparatus of claim 9 wherein said teeth have a height in a range of between about 0.005 and 0.041 centimeters.

11. The apparatus of claim 10 wherein a ratio of the diameter of the opening to the height of the teeth is in a range of between about 7:1 and 320:1.

12. The apparatus of claim 11 wherein the apparatus further includes a seal affixed at the first end of the tube for preventing passage of pressurized gas from the tube through the first end.

13. The apparatus of claim 5 wherein a ridge is disposed circumferentially around the opening for holding said hemostatic agent in place within said tube until plunger for directing said hemostatic agent from said tube is applied to said hemostatic agent.

14. The apparatus of claim 13 wherein said ridge has a height in a range of between about 0.005 and 0.041 centimeters.

15. The apparatus of claim 5 wherein a seal is affixed to the plunger for directing said hemostatic agent from the tapered tube for preventing passage of the hemostatic agent from said tube across said means for directing the hemostatic agent from the tapered tube.

16. The apparatus of claim 5 wherein a seal is affixed to the plunger for directing said hemostatic agent from the tapered tube for preventing passage of pressurized gas from said tube.

17. The apparatus of claim 15 wherein said seal is a gasket.

18. The apparatus of claim 15 wherein said seal is an o-ring.

19. An apparatus for applying a microfibrillar collagen onto a tissue, comprising:

a) a tube having a first end and a second end, wherein a lumen defined by said tube is tapered uniformly from said first end to said second end;

b) a microfibrillar collagen within said tube;

c) plunger for directing said microfibrillar collagen from said tube through an opening at said second end; and d) a seal to prevent passage of the microfibrillar collagen from said tube between said plunger for directing the collagen from the tube and said lumen.

20. The apparatus of claim 19 wherein said opening of said second end has at least one tooth disposed around the opening for holding said collagen in place until plunger for directing said collagen from said tube is actuated to displace said collagen from the tapered tube through said second end.

21. The apparatus of claim 19 wherein a ridge is disposed circumferentially around the opening for holding said collagen in place within said tube until plunger for directing said collagen from said tube is applied to said collagen.

22. An apparatus for applying hemostatic agent onto a tissue, comprising:

a) a tube having a first end and a second end, said tube defining a lumen that is tapered from said first end to said second end;

b) a hemostatic agent within said tube;

c) plunger for directing said hemostatic agent from said tube through an opening at said second end; and d) a seal to prevent passage of a pressurized gas through the first end from said tube between said plunger for directing the hemostatic agent from the tube and said lumen.

23. The apparatus of claim 22 wherein said opening of said second end has at least one tooth disposed around the opening for holding said hemostatic agent in place until plunger for directing said hemostatic agent from said tube is actuated to displace said hemostatic agent from the tapered tube and through said second end.

24. The apparatus of claim 22 wherein a ridge is disposed circumferentially around the opening for holding said hemostatic agent in place within said tube until plunger for directing said hemostatic agent from said tube is applied to said hemostatic agent.

25. The apparatus of claim 22 wherein a displaceable cover is at the opening at said second end.

\* \* \* \* \*